United States Patent
Burnett et al.

[11] Patent Number: 6,026,987
[45] Date of Patent: Feb. 22, 2000

[54] AROMA DISPENSING SYSTEM

[76] Inventors: Sean C. Burnett; Stephen M. Burnett, both of 6515 Hunters West, Apt. 204, Westland, Mich. 48185

[21] Appl. No.: 08/853,444

[22] Filed: May 9, 1997

[51] Int. Cl.⁷ .................................................... G04C 23/00
[52] U.S. Cl. .............................................. 222/78; 222/648
[58] Field of Search ............................. 222/78, 192, 638, 222/639, 642, 644, 645, 646, 647, 648

[56] References Cited

U.S. PATENT DOCUMENTS

| | | | |
|---|---|---|---|
| 4,171,754 | 10/1979 | Rosado | 222/78 X |
| 4,671,435 | 6/1987 | Stout et al. | 222/646 |
| 5,297,988 | 3/1994 | Nishino et al. | 222/644 X |
| 5,321,669 | 6/1994 | Thayer et al. | 222/638 X |
| 5,535,921 | 7/1996 | Gelman et al. | 222/78 |

*Primary Examiner*—Andres Kashnikow
*Assistant Examiner*—Sean P. O'Hanlon
*Attorney, Agent, or Firm*—Donald P. Gillette

[57] ABSTRACT

A system for informing potential customers in a sales space of the availability and aroma of an aromatic material by automatically dispersing controlled amounts of the material from a mannequin only when people are sensed to have moved to within a certain proximity with respect to the mannequin. The purpose of causing a limited amount of the material then to be pumped inoffensively into the air is to make those people pleasantly aware of the aroma in the hope that they will be favorably impressed with it and will become actual customers. The system includes a proximity sensor, a pump controlled by the sensor to dispense the aroma through vents in the surface of the mannequin, and a timer to allow the pump to operate only for a certain length of time at each dispersal, no matter how long a person remains within that proximity, and only during certain time limits of the day and certain days of the week.

10 Claims, 1 Drawing Sheet

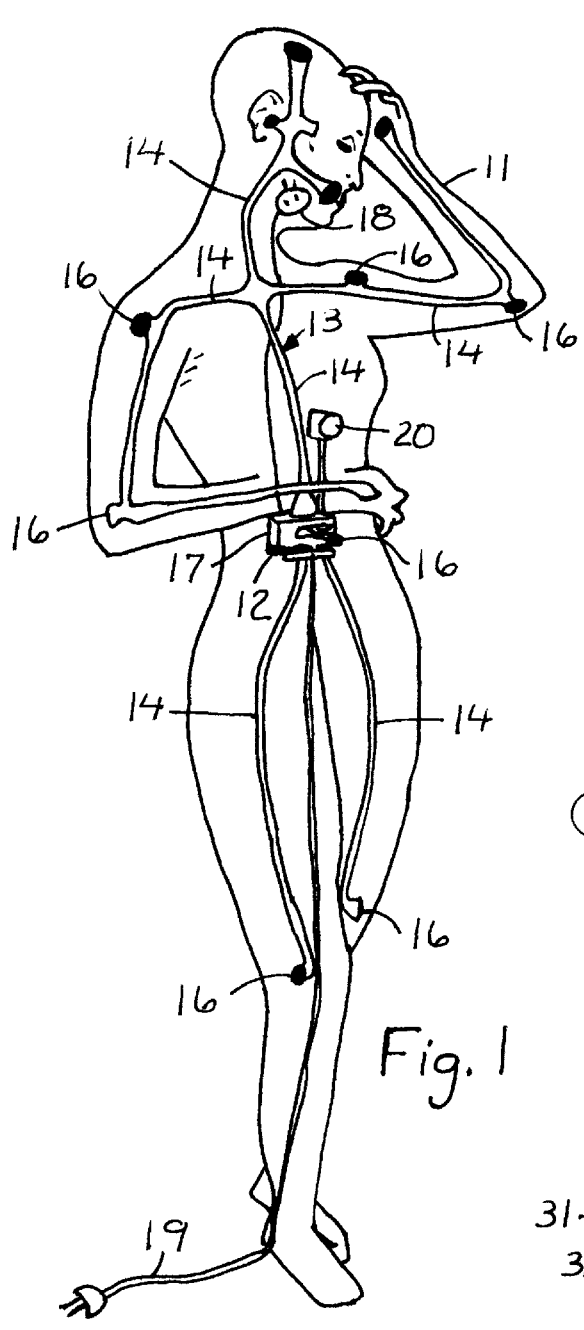
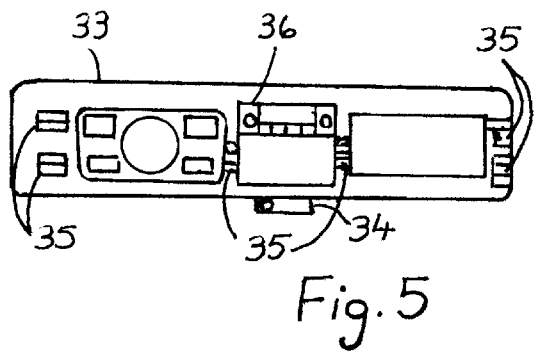
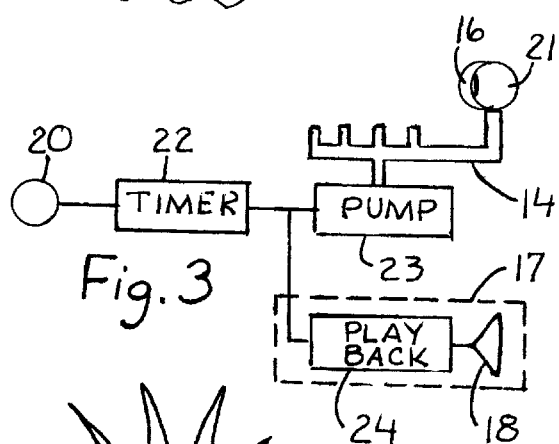
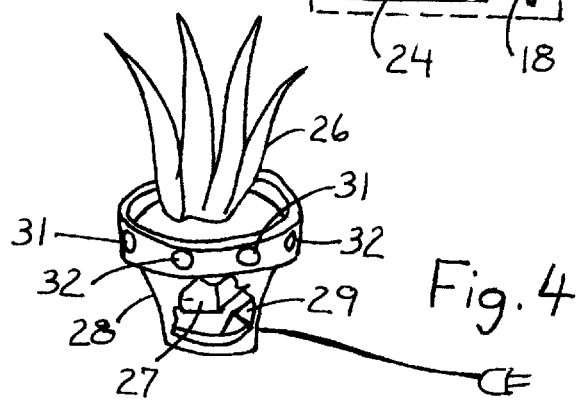

AROMA DISPENSING SYSTEM

BACKGROUND OF THE INVENTION

1. Field of the Invention

This invention relates to the field of aroma dissemination and particularly to an automatic system and method for the controlled dissemination of aromas.

2. The Prior Art

Manufacturers of personal fragrances, such as perfumes and colognes and the like have found it beneficial to use attractive people, called aroma models, in a direct connection between the advertising and sale of their products. Aroma models employed in stores that carry higher priced fragrances, have the task of applying to themselves the fragrance of their employer and then of attempting to intercept, gracefully, as many fragrance buyers as possible from among all persons entering the store or the fragrance sales area. The aroma models attempt not only to call their employer's fragrance to the attention of those potential customers but, simultaneously, to attempt to inform the customers of the trade name of the fragrance. In this way, customers will gain a favorable impression of the fragrance and will know the trade name to ask for at the appropriate counter or other sales location. This technique is used almost exclusively in the sales periods in which such fragrances are most likely to be bought, such as Valentine's Day, Mothers'Day, and Christmas.

One of the disadvantages of this sales technique is that there are sometimes too many aroma models clustered in a small area, since each one wants to have the most advantageous post. Many potential customers dislike such crowding. In addition, having the aroma models close together makes it likely that their fragrances will mingle and will not be sufficiently distinct to convey to passersby the message the fragrance manufacturers desire. In fact, it is possible that mixing the fragrances will result in an aroma that is noticeably less pleasant than any one of the fragrances.

Yet another disadvantage is that, in an effort to stand out, an aroma model may reapply the fragrance too often, achieving an excessively strong smell and using too much of an expensive perfume.

Still another problem is that, while there are certain sales periods when a large number of customers buy aromatic products, there is a steady sale at a lower volume level to customers who buy such products for their own use and for birthday and other gift purposes that occur throughout the year. This volume level is not high enough to justify employing aroma models full time, but manufacturers and store owners would like to make this relatively steady sales level as high as possible.

Another use of aromas that has recently been found to be beneficial is for therapeutic purposes. Aroma therapy can create an improved condition in those who use it, even though they do so entirely alone. One problem in such use is attempting to obtain an appropriate rate of dissemination of the aroma, there being no advantage, and even a possible disadvantage, in dispersing too much of the aroma into a treatment space. It is wasteful to dispense the aroma either before the people seeking treatment enter the treatment space or after they leave it. At the same time, it is clearly undesirable to fail to dispense any of the aroma when a person seeking its benefit is in the treatment space. Having a knowledgeable person set an appropriate rate of dissemination is necessary, but it would be unacceptably expensive for the overwhelming majority of people undergoing aroma therapy to have to rely on having someone constantly on duty to monitor that rate.

OBJECTS AND SUMMARY OF THE INVENTION

It is an object of this invention to provide a system for automatic dissemination of an aroma according to the presence of people likely to be favorably affected by the aroma.

Another object is to provide a climate controlling display system that can be used in retail stores, hospitals, schools, etc. for dispensing aromas for purposes appropriate to the location of the system.

A further object is to provide an aroma dispensing system controlled according to the use of the aroma.

Yet another object of the invention is to space sources of aromas so that the aromas will not conflict with each other to the detriment of all.

Still another object is to connect the dispersal of a fragrance with the transmission of information of a location where the fragrance can be purchased.

It is a particular object of the invention to provide a system for controlled dissemination of an aroma, such system including a source of aromatic material along with pump means to disperse the aromatic material into the atmosphere and means to control the rate and timing of dispersal of the aromatic material.

Those who are skilled in the technology with which this invention deals will recognize further objects after studying the following description.

In accordance with this invention, a source of aromatic fluid is connected to a pump capable of dispensing the aroma into the surrounding atmosphere at a selected rate. A proximity detector responsive to the presence of people is connected to the pump to actuate it when the number of people in the vicinity is sufficiently high to justify emission of the aroma. Measuring means are also connected to the pump or the detector to limit excessive or too frequent emission of the aroma.

The invention will be described in greater detail in connection with the drawings, in which like serial numbers in different figures indicate the same item.

BRIEF DESCRIPTION OF THE DRAWINGS

FIG. 1 shows a system within a mannequin for the distribution of aromas in accordance with this invention.

FIG. 2 shows a fragment of the mannequin in FIG. 1 with one form of vent for use in the dispensing system.

FIG. 3 is a schematic diagram of the operating components of the system in FIG. 1.

FIG. 4 shows an artificial plant used as an enclosure for an aroma dispensing system in accordance with this invention.

FIG. 5 is a simplified representation of the dashboard of a vehicle equipped with an aroma distribution system in accordance with this invention.

DETAILED DESCRIPTION OF A PREFERRED EMBODIMENT

FIG. 1 shows a mannequin 11 of a type suitable for use in a store. Such mannequins are typically opaque and are dressed in a fashion suitable to the display. However, in this instance, the mannequin 11 is transparent in order to display components of an aroma distribution system within it. These components include an electrically operated system 12 that includes an aromatic diffuser connected to a distribution system 13 comprising a plurality of tubes 14 to distribute the aroma of a selected fragrance material as an aromatic mist to any one or more of a plurality of vents 16. The vents are located at sites that cause the aromatic mist to be distributed throughout the space surrounding the mannequin so that anyone approaching the mannequin from any direction will be enveloped in the mist. The mist consists of such exceedingly fine particles of aromatic material that it is not visible.

The mannequin 11 would normally be placed at a location convenient to a sales area of the fragrance material contained within the diffuser. Any customer moving in that general direction, whether or not for the original purpose of buying a fragrance material, would be made aware of the fragrance emanating from the mannequin. At the same time, the customer, would be at the location where the material could be purchased. However, it is not necessary that the mannequin be so placed; it could be in a higher traffic area of the store and could identify the fragrance material audibly or by visible display of the name on calling cards or a sign. For this purpose, the electrical system 12 includes recording means connected to sound reproduction means 17 including a small speaker 18 located near the mouth of the mannequin. Electric power may be supplied to electrical components in the mannequin from a battery or by way of an electric power cord 19 that can be plugged into a convenient outlet. The electrical system in this embodiment also includes sensing means 20 to sense the presence of potential customers in an area close enough to be reached by the aromatic mist. While only a single sensor 20 is shown in the figure, and it is placed to detect the approach of people from the front, there may be other sensors to detect the approach of potential customers from other directions. The sound reproduction means can also be controlled by the sensing means 20 so that the mannequin will speak only when there is someone sufficiently close and will neither waste the aroma nor simply repeat its message into vacant space, thereby wasting the fragrance material and completely losing the realism to be derived from speaking only when there is someone in a position to hear.

FIG. 2 shows a fragment of the mannequin 11 enlarged to make one of the vents 16 visible. This vent is shown as having a sliding cover that can close off all or part of the opening that constitutes the vent 16. While this cover is shown as being a sliding plate, preferably of the same color (if any) as the adjacent part of the surface of the mannequin, the vent could be of a different nature. For example, the vent 16 might be part of an article of jewelry, not only to hide its purpose as a vent, but as a means of attracting attention to the jewelry. It is not always desirable to have all of the vents 16 fully open. In some instances one or more of the vents could be covered by certain articles of clothing placed on the mannequin, which would prevent the aromatic mist from the vents 16 covered by clothes or anything else from reaching the space occupied by potential customers. Due to the fact that the mannequin would normally not be constructed for a specific location, some of the vents 16 may be facing away from the space likely to be occupied by customers, and any aromatic mist allowed to escape through those vents would be wasted. The vent 16 shown in FIG. 2, like all of the other vents in FIG. 1, has a sliding hatch 21 that may be moved anywhere from a fully closed position, in which it completely covered the vent 16, to fully open, in which it covered little or none of the vent. The hatch is shown covering about three-fourths of the vent area. The extent to which each vent 16 is covered can be determined at the time the mannequin is set up at a given location and with a given attire and is not likely to need to be changed very soon thereafter.

FIG. 3 shows a schematic diagram of the electrical components in the system in FIG. 1. In this system, the sensing means 20 is connected to a timer 22 that, in turn, is connected to a diffusing pump 23 to generate the aromatic mist from essential oils or other means for producing such mist. The sensor may be a motion sensor, such as the Rad Motion Sensor STL-10 Sold by Brightmore Electrical Supply Co. of Inkster, Mich., but many other forms of sensors can also be used. A motion sensor could be used to detect the approach of a person, and it could also be used to detect movement of the person in the area within which the sensor would be effective. Such movement could also be a movement away from the sensor, and one way to set up the system in FIG. 3 would be to have it turn on the pump while any motion was being detected and to turn the pump off as soon as no movement was being detected. In order to continue to supply the aromatic mist as long as a person was in the vicinity, even though sitting or standing still, the sensor could be made sensitive to presence as well as motion and would continue to actuate the pump 23 when anyone was detected as being present, whether moving or not.

The timer 22 can be used to prevent an excessive amount of aromatic mist from being pumped out. The length of time for a given amount of mist to dissipate sufficiently to be undetectable can be determined for any essential oil or other type of aromatic material, and the timer can be set to prevent the pump 23 from recycling until the most recent quantity of mist has had time to disappear.

Another use of the timer is to prevent any mist from being generated during periods of low sales activity, or at least to limit the amount of mist generated at such times, for example by requiring the sensing means 20 to indicate a higher level of activity during periods of low sales activity. In large retail stores, peak sales periods are typically between about 1:00 p.m. and 3:00 p.m. and between 5:00 p.m. and 7:00 p.m., and peak sales days are typically Thursday through Sunday. Periods of low sales are typically between 10:00 a.m. and noon, between 3:00 p.m. and 5:00 p.m., and between 7:30 p.m. and 9:00 p.m. (or closing time). Low sales days are typically Monday through Wednesday. It is also possible to set the sensing means to respond to lower activity except in the times of the year when sales of personal fragrances peak.

The timer 22 is also shown connected to a playback machine 24 to produce an audible message by way of the speaker 18 more or less simultaneously with the generation of an aromatic mist. The control signal from the timer to the playback machine need not cause the message to be repeated exactly synchronously with the dispensing of the aromatic mist; it may be repeated less frequently to avoid annoying potential customers who are standing in the area.

FIG. 4 shows another embodiment of the invention in which the mannequin 11 in FIG. 1 is replaced by an item of room decoration, in this case a potted plant 26. The plant can either be real or imitation. If it is real, it is placed in an inner container 27 within an outer container 28, and a pumping mechanism 29 may be located in the space between the inner and outer containers. At least one sensor 31 is located somewhere in the vicinity of the outer container. In this case, there are several sensors in the upper rim, and they are aimed in different directions to sense the presence of anyone anywhere near the container 28. The container 28 has several vents 32 through which the therapeutic aroma may be emitted. This type of arrangement is only one of many that can be used to dispense aromas from an unobtrusive source.

Another place where aroma therapy can be highly beneficial is in a motor vehicle to dispense an aroma that will tend to relax the driver's tension. FIG. 5 shows the dashboard 33 of a vehicle equipped with an aroma therapy system 34 in accordance with this invention. The system is incorporated in the ventilation system that blows heated or cooled air into the vehicle. The aroma can thus be dispensed through the same outlets 35 as heated and cooled air. This system does not need a sensing device; it can be operated from the same part of the electrical system to which such components as the vehicle radio 36 are connected. Thus, it can be turned on when the ignition key (not shown) is actuated. In addition, the system 34 need not have a playback device, since the vehicle radio serves that purpose. However, it is important that the amount of therapeutic aroma be controlled to prevent relaxation of any tension in the driver from being carried too far. Therefore, in addition to a timer of the type illustrated by the timer 22 in FIG. 3, the aroma system 34 has a switch 37 to turn it off.

The invention has been described in terms of specific embodiments, but it will be apparent to those skilled in the technology with which this invention deals that the concept may be embodied in other forms without departing from the true scope of the invention.

What is claimed is:

1. A system for informing potential customers in a sales space of availability and aroma of an aromatic material by controlled dissemination of the aroma in that space, said system comprising:
   (a) a mannequin shaped like a human being;
   (b) a source of the aromatic material;
   (c) a plurality of vents on the surface of the mannequin, each vent aimed in a selected direction;
   (d) a vapor distribution system connecting the source to the vents to distribute the aromatic material thereto, the distribution system comprising:
      a plurality of tubes to distribute the aroma of a selected fragrance material as an aromatic mist to the vents,
      (ii) pump means to produce a pressure differential between the source and the vents to disperse the aromatic material from the source through the vents into the atmosphere adjacent the mannequin, and
      (iii) controllable vent-closure means to control the effective size of the vents;
   (e) proximity sensing means connected to the distribution system to activate the pump means in response to sensing the approach of a person to within a selected proximity of the sensing means; and
   (f) means to initiate dispersal of the aromatic material only in response to the entry of the person into the space, and wherein the aromatic material does not continue to be dispensed due to the continued presence of the person in the space.

2. A system for controlled dissemination of an aroma in accordance with claim 1 in which the means to control the rate and timing of dispersal of the aromatic material comprises timing means controllable to actuate the pump means only on selected days.

3. A system for controlled dissemination of an aroma in accordance with claim 1 in which the means to control the rate and timing of dispersal of the aromatic material comprises timing means controllable to limit the frequency and duration of operation of the pump means.

4. A system according to claim 1 in which the means to control the rate and timing of dispersal of the aromatic material comprises measuring means to limit emission of the aroma to a predetermined maximum amount in a predetermined interval of time.

5. A system for controlled dissemination of an aroma in accordance with claim 1 comprising: a sound reproduction system connected to the proximity sensing means to be actuated thereby to play back a recorded sales message in response to the person's entry into the selected proximity.

6. A system according to claim 1 comprising, in addition: a sound reproduction system connected to the proximity sensing means to reproduce a recorded message only when the sensing means senses entrance of a predetermined number of people into the selected proximity.

7. A system according to claim 6 in which the sound reproduction system is connected to the means to control the rate and timing of dispersal of the mist of the aromatic material to limit excessive repetition of a message as long as the proximity sensing means fails to sense entrance of anyone into the selected proximity.

8. A system for controlled dissemination of an aroma of an aromatic material in a sales space to inform potential customers of the aroma and availability of the material, said system comprising:
   (a) a mannequin in the space;
   (b) a source of the aromatic material;
   (c) a plurality of vents on the mannequin, each aimed in a selected direction;
   (d) a vapor distribution system comprising(i):
      (i) a plurality of tubes connecting the source to the vents to distribute the aromatic material to the vents, and
      (ii) pump means to distribute the aromatic material to the vents and to disperse a mist of the aromatic material through the vents into a predetermined space around the mannequin;
   (e) proximity detection means to detect entry of a person into the space; and
   (f) means to initiate dispersal of the mist of the aromatic material only in response to the entry of the person into the space, and wherein the aromatic material does not continue to be dispensed due to the continued presence of the person in the space.

9. A system for controlled dissemination of an aroma in accordance with claim 8 in which the proximity detection means comprises motion-sensing means.

10. A system according to claim 8 comprising:
    sound reproduction means connected to the proximity detecting means and comprising a speaker in the region of the head of the mannequin to emit sound only when the detecting means detects that the person is sufficiently close to the mannequin to actuate the proximity detection means.

* * * * *